United States Patent [19]

Chen et al.

[11] Patent Number: 5,760,232
[45] Date of Patent: Jun. 2, 1998

[54] SYNTHESIS OF INTERMEDIATES USEFUL IN PREPARING BROMO-SUBSTITUTED TRICYCLIC COMPOUNDS

[75] Inventors: Xing Chen, Plainsboro; Marc Poirier, Parlin; Yee-Shing Wong, Florham Park; Guang-Zhong Wu, Somerville, all of N.J.

[73] Assignee: Schering Corporation, Kenilworth, N.J.

[21] Appl. No.: 882,753

[22] Filed: Jun. 16, 1997

[51] Int. Cl.$^6$ ................................................. C07D 221/16
[52] U.S. Cl. ........................................................... 546/93
[58] Field of Search ............................................. 546/93

[56] References Cited

U.S. PATENT DOCUMENTS 5,151,423 9/1992 Piwinski et al. .................... 546/93

*Primary Examiner*—Amelia Owens
*Attorney, Agent, or Firm*—Anita W. Magatti

[57] ABSTRACT

The invention relates to a process for preparing a compound of the formula

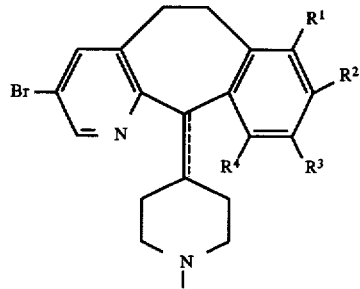

comprising: (a) reacting 2,5-dibromo-3-methylpyridine with an amine of the formula NHR$^5$R$^6$ to obtain an amide;

(b) reacting the amide with a compound of formula 3

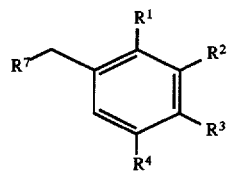

in the presence of a strong base to obtain a compound of formula 4

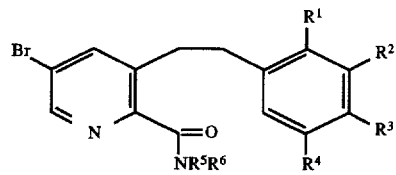

(c) converting a compound of formula 4 to the corresponding cyano compound or aldehyde;

(d) reacting the cyano compound or aldehyde with a piperidine derivative to obtain an aldehyde or alcohol of formula 7a or 7b, respectively:

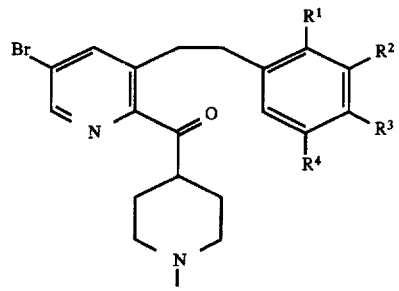

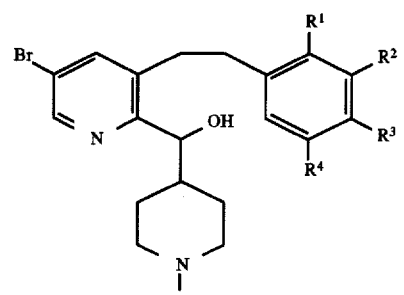

(e) cyclizing a compound of formula 7a or 7b; wherein R$^1$-R$^7$ are as defined in the specification.

9 Claims, No Drawings

SYNTHESIS OF INTERMEDIATES USEFUL IN PREPARING BROMO-SUBSTITUTED TRICYCLIC COMPOUNDS

BACKGROUND OF THE INVENTION

This invention provides an improved process for preparing intermediates useful in the preparation of bromo-substituted tricyclic compounds known as antihistamines and as inhibitors of farnesyl protein transferase (FPT). In particular, the compounds of this invention are useful in the preparation of antihistamines such as those disclosed in U.S. Pat. No. 5,151,423, and of FPT inhibitors disclosed in International Application No. PCT/US96/19603, filed Dec. 19, 1996.

SUMMARY OF THE INVENTION

This invention provides a process for preparing a compound of the formula

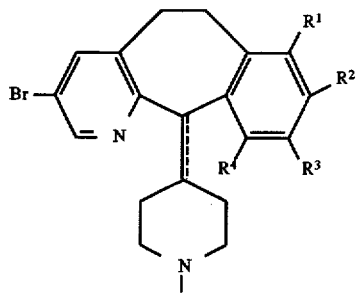

wherein:

$R^1$, $R^2$, $R^3$ and $R^4$ are independently selected from the group consisting of hydrogen and halo, provided that at least one of $R^1$, $R^2$, $R^3$ and $R^4$ is hydrogen and at least one of $R^1$, $R^2$, $R^3$ and $R^4$ is halo; and the dotted line represents an optional double bond; comprising:

(a) reacting a compound of formula 1

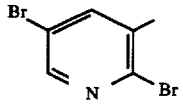

(i) with an amine of the formula $NHR^5R^6$, wherein $R^5$ is hydrogen and $R^6$ is $C_1$–$C_6$ alkyl, aryl or heteroaryl; $R^5$ is $C_1$–$C_6$ alkyl, aryl or heteroaryl and $R^6$ is hydrogen; $R^5$ and $R^6$ are independently selected from the group consisting of $C_1$–$C_6$ alkyl and aryl; or $R^5$ and $R^6$, together with the nitrogen to which they are attached, form a ring comprising 4 to 6 carbon atoms or comprising 3 to 5 carbon atoms and one hetero moiety selected from the group consisting of —O— and —$NR^9$—, wherein $R^9$ is H, $C_1$–$C_6$ alkyl or phenyl; in the presence of a palladium catalyst and carbon monoxide to obtain an amide of formula 2:

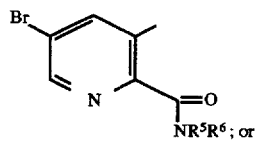

(ii) with an alcohol of the formula $R^{10}OH$, wherein $R^{10}$ is $C_1$–$C_6$ lower alkyl or $C_3$–$C_6$ cycloalkyl, in the presence of a palladium catalyst and carbon monoxide to obtain the ester of formula 2A

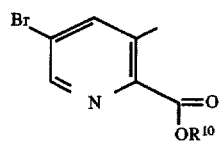

followed by reacting the compound of 2A with an amine of formula $NHR^5R^6$ to obtain the amide of formula 2;

(b) reacting the amide of formula 2 with a compound of formula 3

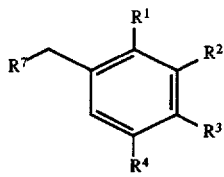

wherein $R^1$, $R^2$, $R^3$ and $R^4$ are as defined above and $R^7$ is Cl or Br, in the presence of a strong base to obtain a compound of formula 4

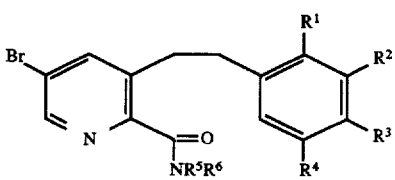

(c)(i) converting a compound of formula 4 to a cyano compound of formula 5a

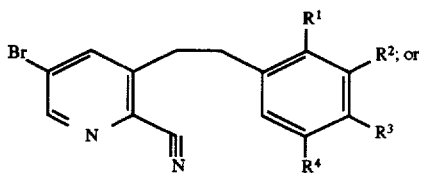

(c)(ii) converting a compound of formula 4 or a cyano compound of formula 5a to an adlehyde of formula 5b

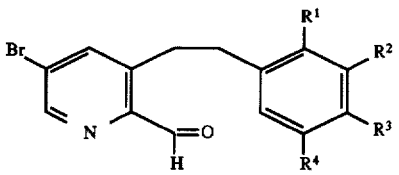

(d) reacting compound 5a or 5b with a piperidine derivative of formula 6

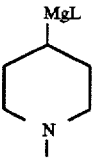

wherein L is a leaving group selected from the group consisting of Cl and Br, to obtain a ketone of formula 7a or an alcohol of formula 7b, respectively:

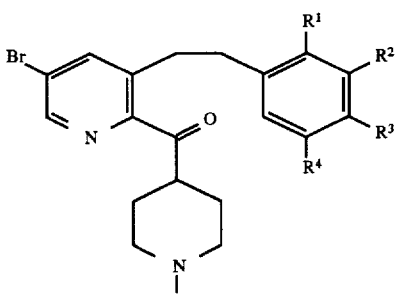

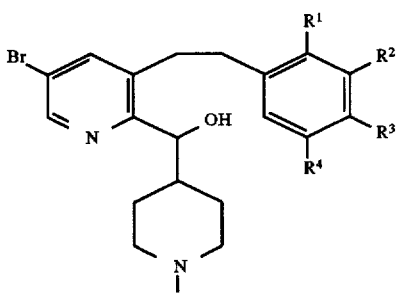

(e)(i) cyclizing a compound of formula 7a to obtain a compound of formula I wherein the dotted line represents a double bond; or (e)(ii) cyclizing a compound of formula 7b to obtain a compound of formula I wherein the dotted line represents a single bond.

Preferred compounds of formula I are those wherein $R^2$ is halo. Also preferred are compounds wherein $R^1$ and $R^3$ are each hydrogen. Another group of preferred compounds is that wherein $R^1$, $R^3$ and $R^4$ are hydrogen and $R^2$ is halo. Still another group of preferred compounds is that wherein $R^1$ and $R^3$ are each hydrogen and $R^2$ is halo. Yet another group of preferred compounds is that wherein $R^1$ and $R^3$ are each hydrogen and $R^2$ and $R^4$ are independently selected from the group consisting of halo. Halo is preferably Cl or Br.

DETAILED DESCRIPTION

As used herein, the term "lower alkyl" means straight or branched alkyl chains of 1 to 6 carbon atoms.

"Halo" refers to fluorine, chlorine, bromine or iodine radicals.

"Aryl" means phenyl, substituted phenyl wherein the substituents are 1 to 3 substituents independently selected from the group consisting of $C_1$ to $C_6$ alkyl and $C_1$ to $C_6$ alkoxy, benzyloxy or naphthyl.

"Heteroaryl" means a 5- or 6-membered aromatic ring comprising one or two nitrogen atoms, e.g., pyridyl, pyrimidyl, imidazolyl or pyrrolyl.

When $R^5$ and $R^6$, together with the nitrogen to which they are attached, form a ring comprising 4 to 6 carbon atoms, the rings so produced are exemplified by pyrrolidinyl, piperidinyl and perhydroazepine. When $R^5$ and $R^6$, together with the nitrogen to which they are attached, form a ring comprising 4 to 5 carbon atoms and a heteroatom, the rings so produced are exemplified by piperazinyl, N-methyl-piperazinyl, N-phenyl-piperazinyl and morpholinyl.

The compounds prepared by the process disclosed above are useful as intermediates in the procedures described in PCT/US96/19603 and U.S. Pat. No. 5,151,423 to obtain the desired compounds wherein the piperidinyl ring is N-substituted. By using the 3-bromo-substituted intermediates prepared by the process of this invention, the desired tricyclic antihistamines and FPT inhibitors described above can be made by an eleven-step process rather than the fifteen-step process disclosed in the art.

Compounds of formula I can be converted to other compounds of formula I by methods known in the art, i.e., compounds wherein $R^1$, $R^2$, $R^3$ or $R^4$ is hydrogen can be converted to the corresponding compounds wherein $R^1$, $R^2$, $R^3$ or $R^4$ is halogen. Such procedures are shown in PCT/US96/19603, wherein, for example, a compound wherein $R^2$ is Cl, $R^1$, $R^3$ and $R^4$ are hydrogen and the piperidinyl nitrogen is protected by a —$COOCH_2CH_3$ group is reacted with $KNO_3$, the resulting nitro-substituted compound is reduced to the amine, the resulting compound is reacted with $Br_2$ and the amino group is removed to obtain a compound wherein $R^2$ is Cl, $R^4$ is Br and $R^1$ and $R^3$ are hydrogen.

In step (a), the di-bromo-substituted pyridine of formula 1 is reacted with the amine $NHR^5R^6$ in the presence of a palladium catalyst, carbon monoxide (CO) and a base. As defined above, the amines of formula $NHR^5R^6$ are exemplified by t-butylamine, aniline, N-methylaniline, pyrrolidine, piperidine, perhydroazepine, piperazine, N-methylpiperazine, N-phenyl-piperazine and morpholine. Preferred amines are pyrrolidine and t-butylamine, with t-butylamine being most preferred.

Palladium catalysts are exemplified by $Pd(OAc)_2/P(R^{11})_3$ at ratios of 1:1 or 1:2; $(PPh_3)_2PdCl_2$ at a range of 0.5 to 40 mol %, preferably 1 to 10 mol %, and most prefereably 1 to 5 mol %; $Pd(PPh_3)_4$; $(R^{11})_3P/Pd_2(dba)_3$; $Pd(OAc)_2/2,2'$-bipyridine at ratios of 1:1 to 1:2, preferably 1 to 10 mol %; and Pd/C, wherein Ac is acetyl, $R^{11}$ is $C_1$ to $C_6$ alkyl or aryl, Ph is phenyl, and dba is dibenzylidene acetone. Preferred catalysts are $Pd(OAc)_2/P(R^{11})_3$ and $(PPh_3)_2PdCl_2$.

The amount of amine ($NHR^5R^6$) reacted ranges from 1 to 4 equivalents, and is preferably 1 to 1.5 equivalents. Suitable bases include, but are not limited to, $C_1$ to $C_6$ alkyl amines such as triethylamine ($Et_3N$), t-butylamine and 1,8-diazobicyclo[5.4.0]undec-7-ene (DBU), and inorganic bases such as $K_2CO_3$, $Na_2CO_3$, $Na_2HPO_4$ and NaOH. Preferred bases are $K_2CO_3$ and $Et_3N$, with $Et_3N$ being most preferred.

Suitable solvents are tetrahydrofuran (THF), dimethylformamide (DMF), acetonitrile ($CH_3CN$) and toluene or a combination thereof. $CH_3CN$ is preferred for reaction with an amine and a combination of $CH_3CN$ and toluene is preferred for reaction with an alcohol. The temperature range for the reaction is 35° C. to 100° C., preferably about 55° C. for reaction with the amine and preferably about 80° C. for reaction with an alcohol. The reaction is carried out at a pressure of 5 psi to 500 psi, preferably 40 to 200 psi, and most preferably at 50 to 150 psi. The time for reaction ranges from 2 hours to 4 days, preferably 4 hours to 2 days, and most preferably 16 to 48 hours.

Conversion of the ester of formula 2A to the amide of formula 2 is accomplished by methods well known in the art, for example by reacting the ester directly with the amine or by using the conditions described by Basha et al in *Tetrahedron Letters*, (1977), p. 4171.

In step (b), the amide formed in step (a) is reacted with the halomethyl-substituted compound of formula 3 in a solvent such as THF, t-butyl methyl ether (t-BuOMe), diethyl ether ($Et_2O$), diglyme or a mixture thereof, preferably a mixture of THF and t-butyl methyl ether, in the presence of a strong base such as lithium diisopropylamide (LDA), lithium hexamethyldisilylamide or sodium amide, preferably LDA. The concentration of the base ranges from 2.0 to 4.0 equivalents, preferably 2.0 to 2.2 equivalents. The compound of formula 3 is reacted in a concentration range of 1.0 to 1.5 equivalents. preferably 1.1 equivalents. The reaction is carried out in a temperature range of −78° C. to −20° C., preferably −50° C. to −30° C.

In step (c)(i), the product of step (b) is converted to the corresponding cyano compound of formula 5a by reacting with $POCl_3$ or $SOCl_2$ in a solvent such as $CH_2Cl_2$ or without a solvent, preferably without a solvent. The reaction is carried out in a temperature range of 50° C. to reflux, preferably at reflux.

Alternatively, in step (c)(ii), the product of step (b) or step (c)(i) is converted to the corresponding aldehyde of formula 5b by reacting with DIBALH or $LiAlH_4$ and its derivatives, preferably DIBALH, in a solvent such as toluene, THF or t-BuOMe, preferably toluene. The reaction is carried out in a temperature range of −78° C. to −30° C., preferably −78° C. to −50° C.

In step (d), the product of step 5a or 5b is reacted with a piperidine derivative of formula 6 as defined above to obtain a ketone or alcohol, respectively. The reaction is carried out in a solvent such as THF, toluene or t-BuOMe, preferably THF. The concentration of the piperidine derivative ranges from 1.0 to 2.0 equivalents, preferably 1.1 to 1.2 equivalents. The reaction is carried out in a temperature range from −20° C. to 50° C., preferably 35° C. to 45° C., for the product of step 5a, and in a range from −78° C. to 0° C., preferably −78° C. to −60° C., for the product of step 5b.

In step (e)(i), the ketone of formula 7a is cyclized to a compound of formula I wherein the dotted line represents a double bond by treatment with a strong acid such as $CF_3SO_3H$, $CH_3SO_3H$ or $BF_3.HF$, preferably $CF_3SO_3H$, in a temperature range of 50° C. to 120° C., preferably 90° C. to 95° C.

In step (e)(ii), the alcohol of formula 7b is cyclized to a compound of formula I wherein the dotted line represents a single bond by treatment with an acid such as $H_2SO_4$, polyphosphoric acid or $CH_3SO_3H$, preferably polyphosphoric acid, in a temperature range of 100° C. to 200° C., preferably 160° C. to 180° C.

Starting materials of formula 1, 3, 6 and $NHR^5R^6$ are known in the art or can readily be prepared by one skilled in the art.

Following are specific examples of the procedures in the various steps of the process of this invention for preparing compounds of formula 1, although those skilled in the art will appreciate that similar procedures within the scope of the process of this invention can be used to prepare other compounds of formula 1.

EXAMPLE 1

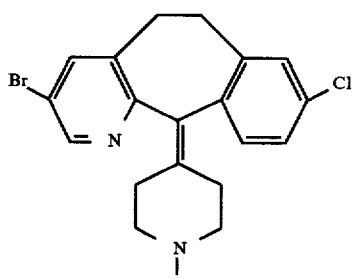

Step (a):

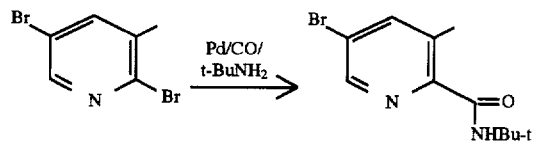

To an autoclave were added 16 g (60.6 mmole) of 2,5-dibromo-3-methylpyridine, 4.5 g (6.4 mmole) of $(Ph_3P)_2PdCl_2$, 150 ml of toluene, 150 ml of $CH_3CN$, and 17 ml (160 mmole) of t-butylamine. The autoclave was sealed, evacuated, purged with nitrogen and charged with carbon monoxide to 120 psi. The reaction mixture was heated to 60° C. for two days with periodical refilling, as necessary, and then cooled to r.t. The contents of the autoclave was vented under vacuum, flushed with nitrogen and transferred to a flask with the aid of water and EtOAc. The mixture was concentrated and filtered through a pad of celite. The filtrate was extracted with EtOAc, the combined extract was washed with brine, dried over $MgSO_4$, filtered and concentrated. The residue was separated by column chromatography to obtain 11 g of the product as an oil, 67% yield. 1H NMR ($CDCl_3$): 8.40 (d, J=2.1, 1H), 7.90 (br, 1H), 7.73 (d, J=2.1, 1H), 2.73 (s, 3H ), 1.48 (s, 9H). $^{13}C$ NMR ($CDCl_3$): 164.53, 146.58, 146.08, 142.92, 136.93, 122.28, 50.86, 28.71, 20.57.

Step (b):

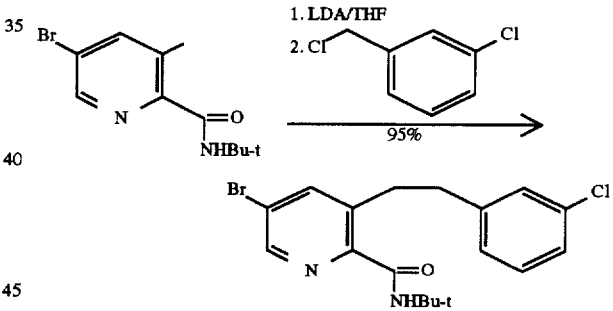

To a solution of 10.56 ml (80.7 mmole) of i-$Pr_2NH$ in 90 ml THF at 0° C. was added 31.20 ml (77.9 mmole) of 2.5M n-BuLi in hexanes and the solution was stirred for 30 min. To the LDA solution was added dropwise a solution of 9.6 g (35.4 mmole) of the product of Step (a) in 45 ml THF at −78° C. The resulting purple solution was stirred at −78° C. for 30 min., at −42° C. for 15 min., and then recooled to −78° C. To this solution was added dropwise a solution of 8.0 g (50 mmole) of 3-chlorobenzyl chloride in 50 ml THF. The reaction was warmed to room temperature over 1 hour. Saturated $NH_4Cl$ solution (50 ml) and ice-water (50 ml) were added to the reaction and the mixture was evaporated to half of the volume under vaccum. Extraction with EtOAc (100 ml×2) and evaporation of the solvent gave 16 g of the desired product, which was used directly in next step. $^1H$ NMR ($CDCl_3$): 8.40 (d, J=2.1, 1H), 7.78 (b, 1H), 7.55 (d, J=2.1, 1H), 7.16 (m, 3H), 7.06 (m, 1H), 3.38 (m, 2H), 2.90 (m, 2H), 1.45 (s, 9H).

Step (c)

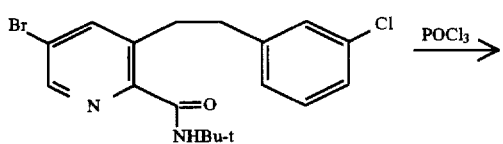

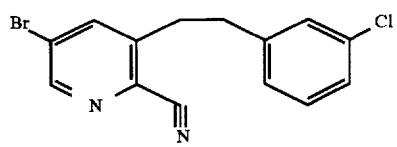

The amide (16 g) of Step (b) was dissolved in POCl₃ (100 ml) and the solution was refluxed for 2.5 hr and then concentrated to a third of its volume under vaccum, poured into 200 g ice and adjusted to pH 8 with 50% NaOH at 25° C. The resultant mixture was stirred for 2 hr at 25° C. and the pH maintained at 8 with NaOH. Extraction with EtOAc (100 ml×2) and evaporation gave a solid residue which was washed with hexane. After drying, 10 g of product was obtained; the yield was 88% in two steps. $^1$NMR (CDCl₃): 8.62 (d, J=2.0, 1H), 7.71 (d, J=2.0, 1H), 7.23 (m, 2H), 7.16 (s,1H), 7.04 (m,1H), 3.11 (m, 2H), 2.95 (m, 2H). $^{13}$C NMR (CDCl₃): 150.21, 142.66, 141.10, 139.97, 134.42, 131.86, 129.96, 128.54, 126.95, 126.63, 124.60, 115.63, 35.94, 34.26.

Step (d)

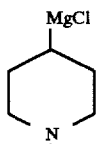

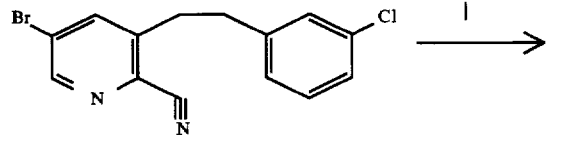

To a solution of the product of Step (c) (2 g, 6.25 mmole) in THF (20 ml) at 40°–45° C. was added dropwise N-methyl-piperidyl magnesium chloride (8 ml, 0.94M, 1.2 eq) and the reaction mixture was stirred for 30 min. The reaction mixture was adjusted to pH 2 with 2N HCl and was stirred for 1 h. The pH was adjusted to 10 with 28% NH₄OH and the mixture was extracted with EtOAc (100 ml×2). The organic layer was separated and concentrated to give a residue, which was passed through silica gel as a CH₂Cl₂ solution. The solvent was removed to obtain an oil (2.3 g). $^1$H NMR (CDCl₃): 8.54 (d, J=2.1, 1H), 7.62 (d, J=2.1, 1H), 7.08 (m, 3H), 7.30 (dt, J=7.0, 1.5, 1H), 3.62 (m, 1H), 3.08 (m, 2H), 2.86 (m, 4H), 2.28 (s, 3H), 2.06 (m, 2H), 1.82 (m, 2H), 1.75 (m, 2H). $^{13}$C NMR (CDCl₃): 205.12, 150.09, 147.62, 142.81, 141.65, 139.37, 134.14, 129.69, 128.59, 126.75, 126.41, 123.17, 55.19, 46.35, 43.73, 36.97, 34.63, 27.93.

Step (e):

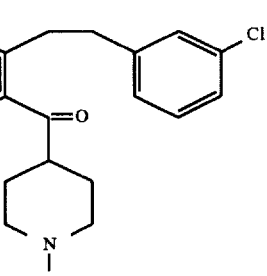

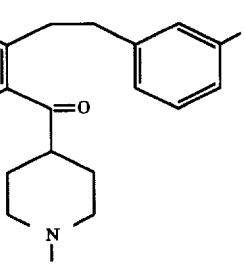

Stir a solution of ~2 g (4.6 mmole) of the product of Step (d) in 4.6 ml (50 mmole) of CF₃SO₃H at 90° C. for 18 hr under nitrogen. Pour the cooled reaction into ice water and adjust to pH 10 with 29% NH₄OH. Extract the product with CH₂Cl₂ (2×) to obtain 2 g residue. Purify by chromatography on a silica gel column, eluting with CH₂Cl₂:CH₃OH:NH₄OH (28%) (100:3:0.1). The yield is 68% based on comsumption of the starting ketone. $^1$H NMR (CDCl₃): 8.44 (d, J=2.2, 1H), 7.56 (d, J=2.2, 1H), 7.12 (m, 3H), 3.36 (m, 2H), 2.70 (m, 4H), 2.50 (m, 1H), 2.35 (m, 3H), 2.25 (s, 3H), 2.05 (m, 2H). $^{13}$C(CDCl₃): 155.79, 147.36, 139.57, 139.12, 137.45, 135.18, 132.78, 131.62, 130.64, 128.77, 126.12, 118.53, 56.74, 45.93, 31.33, 31.30, 30.99, 30.73.

EXAMPLE 2

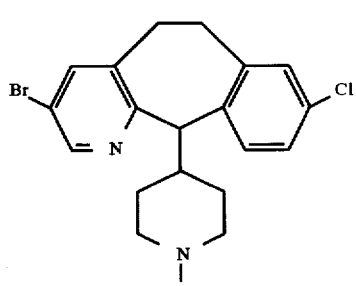

Step 1:

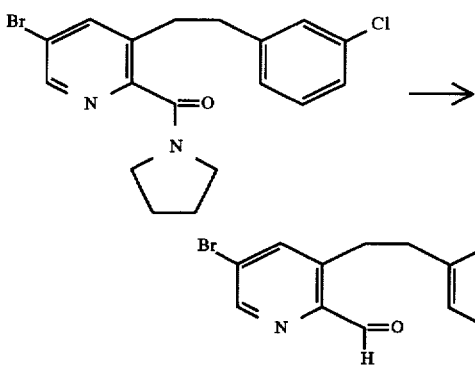

To a solution of the starting amide (8 g, 20.3 mmole) in 80 ml of toluene at −70° C. was added 22 ml (22 mmole in toluene) of DIBALH dropwise over 10 min. The reaction was monitored by TLC; after completion, the reaction mixture was transferred at −60° C. to a quenching solution prepared with 150 ml of water and 11 g of malic acid, with the pH being adjusted to 14 with 50% NaOH. The resultant mixture was stirred for 15 min and the toluene layer was separated. The aqueous layer was extracted with toluene (100 mL), the toluene layers were combined, dried over MgSO$_4$ and filtered. Concentration gave 5.7 g product, 87% yield. $^1$H NMR (CDCl$_3$): 10.10 (s,1H), 8.71 (d, J=2.0, 1H), 7.67 (d, J=2.0, 1H), 7.10–7.20 (m, 4H), 3.25 (m, 2H), 2.85 (m, 2H).

Step 2:

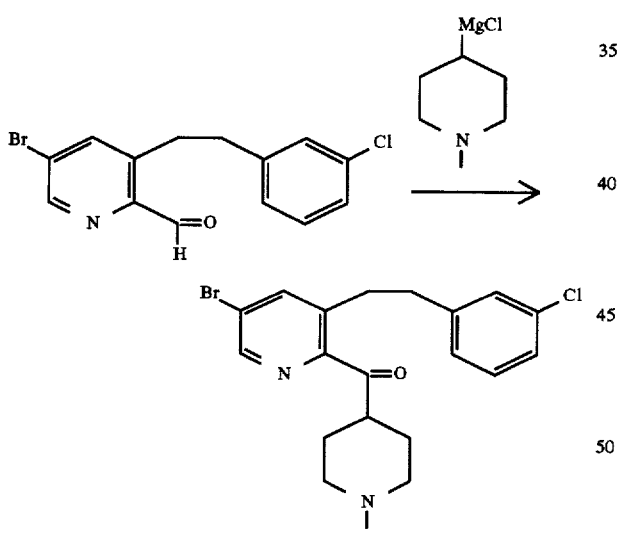

To a mixture of the aldehyde of Step 1 (0.32 g, 0.60 mmol) in THF (20 ml) at −78° C. was added dropwise the Grignard reagent (0.9M, 0.7 ml, 0.63 mmol). After 30 min, aqueous NH$_4$Cl (~2 ml) was added and the mixture was warmed to room temperature. Water (50 ml) was added and the mixture was extracted with EtOAc (50 ml×2 ). After concentrating the combined organic phase, the residue was separated by preparative TLC to give 75 mg of product. $^1$H NMR (CDCl$_3$): 8.49 (d, J=2.1, 1H), 7.66 (d, J=2.1, 1H), 7.51 (d, J=2.3, 1H), 7.05 (d, J=2.3, 1H), 4.69 (d, J=4.50, 1H), 2.70–3.10 (m, 6H), 2.19 (s, 3H), 1.80 (m, 3H), 1.55 (m, 4H), 1.35 (m, 1H).

Step 3:

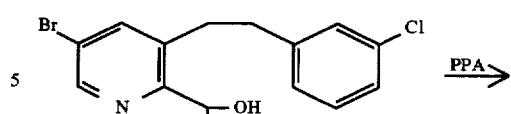

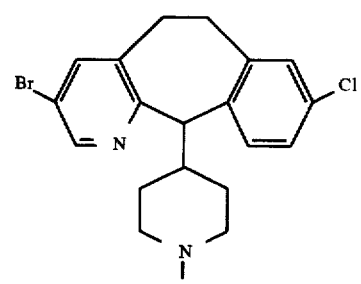

A mixture of 0.5 g of the alcohol from Step 2 with 5 g of polyphosphoric acid was heated to 170° C. for 2 hr. After cooling to r.t., the reaction was adjusted to pH 12 with aqueous NaOH and extracted with EtOAc. The organic layer was combined and dried over MgSO$_4$ and concentrated to give the product. $^1$H NMR (CDCl$_3$): 8.35 (d, J=2.0, 1H), 7.50 (d, 1H), 7.06 (m, 3H), 3.85 (d, J=6.3, 1H), 3.35 (m, 2H), 2.80 (m, 4H), 2.20 (s, 3H), 2.05 (m, 1H), 1.75 (m, 2H), 1.20–1.50 (m, 4H).

We claim:

1. A process for preparing a compound of the formula 1

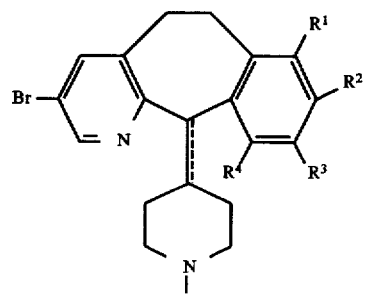

wherein:

R$^1$, R$^2$, R$^3$ and R$^4$ are independently selected from the group consisting of hydrogen and halo, provided that at least one of R$^1$, R$^2$, R$^3$ and R$^4$ is hydrogen and at least one of R$^1$, R$^2$, R$^3$ and R$^4$ is halo; and the dotted line represents an optional double bond; comprising:

(a) reacting a compound of formula 1

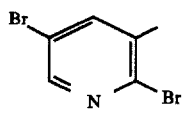

(i) with an amine of the formula NHR$^5$R$^6$, wherein R$^5$ is hydrogen and R$^6$ is C$_1$–C$_6$ alkyl, aryl or heteroaryl; R$^5$ is C$_1$–C$_6$ alkyl, aryl or heteroaryl and R$^6$ is hydrogen; R$^5$ and R$^6$ are independently selected from the group consisting of $C_1$–$C_6$ alkyl and aryl; or $R^5$ and $R^6$, together with the nitrogen to which they are attached, form a ring comprising 4 to 6 carbon atoms or comprising 3 to 5 carbon atoms and one hetero moiety selected from the group consisting of —O— and —$NR^9$—, wherein $R^9$ is H, $C_1$–$C_6$ alkyl or phenyl; in the presence of a palladium catalyst and carbon monoxide to obtain an amide of formula 2:

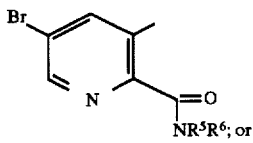
2

(ii) with an alcohol of the formula $R^{10}OH$, wherein $R^{10}$ is $C_1$–$C_6$ lower alkyl or $C_3$–$C_6$ cycloalkyl, in the presence of a palladium catalyst and carbon monoxide to obtain the ester of formula 2A

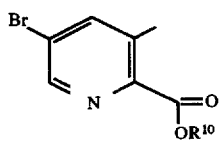
2A followed by reacting the compound of 2A with an amine of formula $NHR^5R^6$ to obtain the amide of formula 2;

(b) reacting the amide of formula 2 with a compound of formula 3

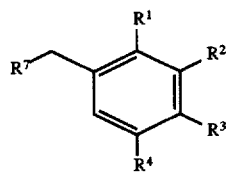
3 wherein $R^1$, $R^2$, $R^3$ and $R^4$ are as defined above and $R^7$ is Cl or Br, in the presence of a strong base to obtain a compound of formula 4

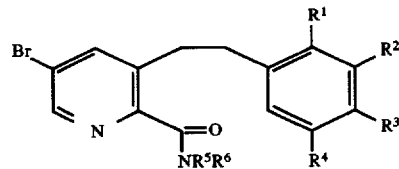
4

(c)(i) converting a compound of formula 4 to a cyano compound of formula 5a

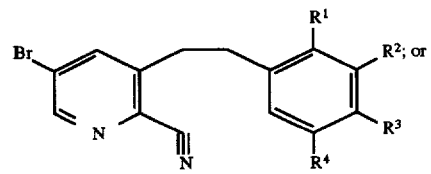
5a (c)(ii) converting a compound of formula 4 or a cyano compound of formula 5a to an aldehyde of formula 5b

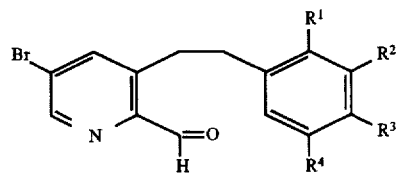
5b (d) reacting compound 5a or 5b with a piperidine derivative of formula 6

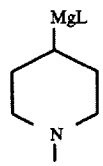
6 wherein L is a leaving group selected from the group consisting of Cl and Br, to obtain a ketone of formula 7a or an alcohol of formula 7b, respectively:

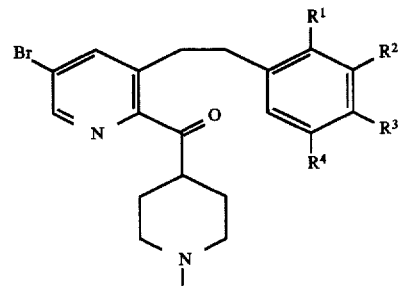
7a

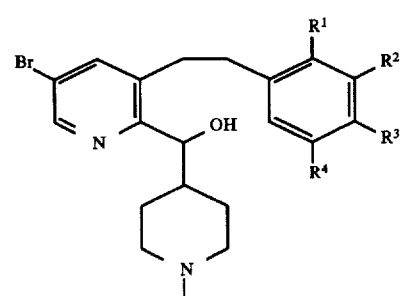
7b (e)(i) cyclizing a compound of formula 7a to obtain a compound of formula 1 wherein the dotted line represents a double bond; or (e)(ii) cyclizing a compound of formula 7b to obtain a compound of formula 1 wherein the dotted line represents a single bond.

2. A process of claim 1 wherein $R^5$ is t-butylamine and $R^6$ is H, or $R^5$ and $R^6$ together are —$(CH_2)_4$—.

3. A process of claim 1 wherein the palladium catalyst is $Pd(OAc)_2/P(R^{10})_3$; $(PPh_3)_2PdCl_2$; $Pd(PPh_3)_4$; $(R^{10})_3P/Pd_2(dba)_3$; or Pd/C, wherein Ac is acetyl, $R^{10}$ is $C_1$ to $C_6$ alkyl or aryl, Ph is phenyl, and dba is dibenzylidene acetone.

4. A process of claim 1 wherein $R^1$ and $R^2$ are independently selected from the group consisting of chloro and bromo, and $R^3$ and $R^4$ are each hydrogen.

5. A process of claim 1 wherein $R^2$ and $R^4$ are independently selected from the group consisting of chloro and bromo, and $R^1$ and $R^3$ are each hydrogen.

6. A process of claim 4 wherein $R^5$ is t-butylamine, $R^6$ is H, and the palladium catalyst is $Pd(OAc)_2/P(R^{11})_3$ wherein Ac is acetyl and $R^{11}$ is $C_1$ to $C_6$ alkyl or aryl.

7. A process of claim 5 wherein $R^5$ is t-butylamine. $R^6$ is H, and the palladium catalyst is $Pd(OAc)_2/P(R^{11})_3$ wherein Ac is acetyl and $R^{11}$ is $C_1$ to $C_6$ alkyl or aryl.

8. A process of claim 1 comprising (a) reacting a compound of formula 1

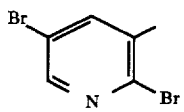
1

(i) with an amine of the formula $NHR^5R^6$, wherein $R^5$ and $R^6$ are as defined in claim 1, in the presence of a palladium catalyst and carbon monoxide to obtain an amide of formula 2:

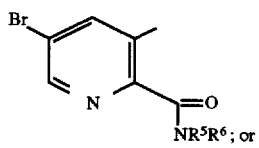
2

(ii) with an alcohol of the formula $R^{10}H$, wherein $R^{10}$ is $C_1$–$C_6$ lower alkyl or $C_3$–$C_6$ cycloalkyl, in the presence of a palladium catalyst and carbon monoxide to obtain the ester of formula 2A

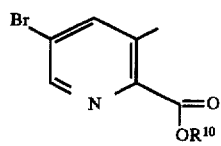
2A followed by reacting the compound of 2A with an amine of formula $NHR^5R^6$ to obtain the amide of formula 2;

(b) reacting the amide of formula 2 with a compound of formula 3

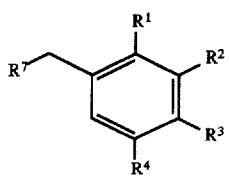
3 wherein $R^1$, $R^2$, $R^3$, $R^4$ and $R^7$ are as defined in claim 1, in the presence of a strong base to obtain a compound of formula 4

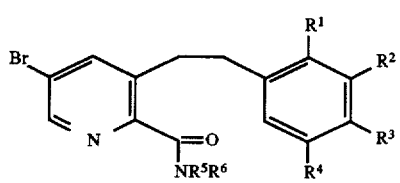
4

(c) converting a compound of formula 4 to a cyano compound of formula 5a

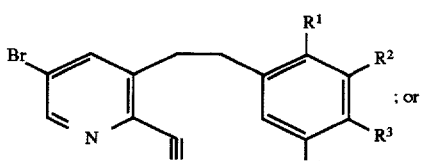
5a (d) reacting compound 5a with a compound of formula 6

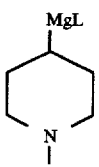
6 as defined in claim 1, to obtain a ketone of formula 7a:

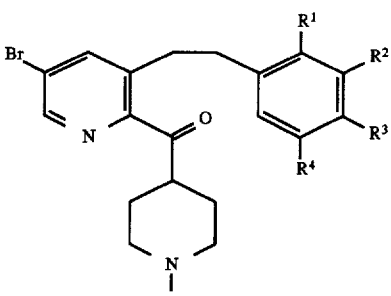
7a (e)(i) cyclizing a compound of formula 7a to obtain a compound of formula 1 wherein the dotted line represents a double bond.

9. A process of claim 1 comprising:

(a) reacting a compound of formula 1

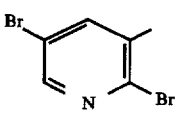
1

(i) with an amine of the formula $NHR^5R^6$, wherein $R^5$ and $R^6$ are as defined in claim 1, in the presence of a palladium catalyst and carbon monoxide to obtain an amide of formula 2:

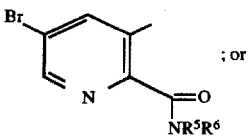
2

(ii) with an alcohol of the formula $R^{10}OH$, wherein $R^{10}$ is $C_1$–$C_6$ lower alkyl or $C_3$–$C_6$ cycloalkyl, in the presence of a palladium catalyst and carbon monoxide to obtain the ester of formula 2A

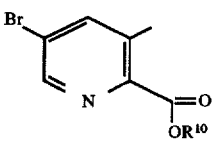
2A followed by reacting the compound of 2A with an amine of formula $NHR^5R^6$ to obtain the amide of formula 2;

(b) reacting the amide of formula 2 with a compound of formula 3

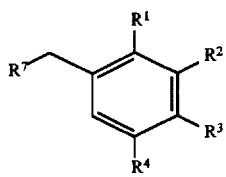

wherein $R^1$, $R^2$, $R^3$, $R^4$ and $R^7$ are as defined in claim 1, in the presence of a strong base to obtain a compound of formula 4

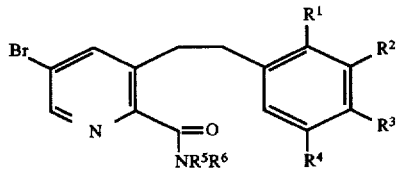

(c)(i) converting a compound of formula 4 to a cyano compound of formula 5a

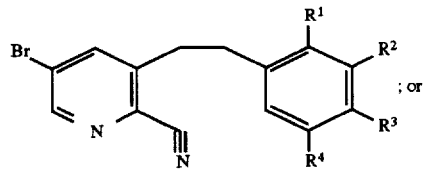

(c)(ii) converting a compound of formula 4 or a cyano compound of formula 5a to an aldehyde of formula 5b

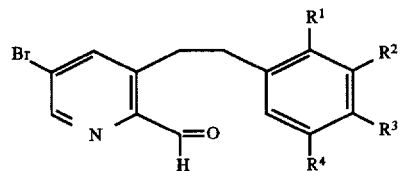

(d) reacting compound 5b with a compound of formula 6

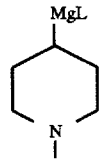

as defined in claim 1, to obtain an alcohol of formula 7b:

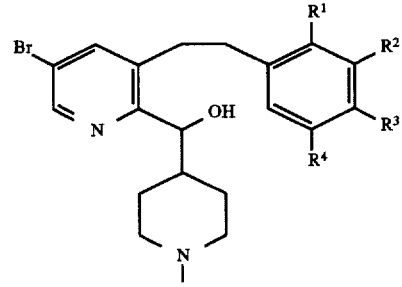

(e)(ii) cyclizing a compound of formula 7b to obtain a compound of formula 1 wherein the dotted line represents a single bond.

* * * * *